(12) United States Patent
Fawcett et al.

(10) Patent No.: US 9,068,947 B2
(45) Date of Patent: Jun. 30, 2015

(54) OPTICAL SYSTEM FOR MULTIPLE REACTIONS

(75) Inventors: Adrian Fawcett, Carlsbad, CA (US); David Tracy, Norwalk, CT (US)

(73) Assignee: PCR Max Limited, London (GB)

( * ) Notice: Subject to any disclaimer, the term of this patent is extended or adjusted under 35 U.S.C. 154(b) by 180 days.

(21) Appl. No.: 13/132,315

(22) PCT Filed: Dec. 3, 2009

(86) PCT No.: PCT/US2009/066645
§ 371 (c)(1),
(2), (4) Date: Jul. 6, 2011

(87) PCT Pub. No.: WO2010/065779
PCT Pub. Date: Jun. 10, 2010

(65) Prior Publication Data
US 2011/0263455 A1   Oct. 27, 2011

Related U.S. Application Data

(60) Provisional application No. 61/119,692, filed on Dec. 3, 2008.

(51) Int. Cl.
*G01N 21/03* (2006.01)
*G02B 5/04* (2006.01)
*C12Q 1/68* (2006.01)
*G01N 21/64* (2006.01)
*B01L 3/00* (2006.01)

(52) U.S. Cl.
CPC ........ *G01N 21/6452* (2013.01); *G01N 21/0332* (2013.01); *G02B 5/045* (2013.01); *G02B 5/04* (2013.01); *G01N 21/0303* (2013.01); *C12Q 1/686* (2013.01); *B01L 3/50851* (2013.01); *G01N 2021/6417* (2013.01); *G01N 2021/6463* (2013.01)

(58) Field of Classification Search
CPC ............. G01N 1/68; G02B 5/04; G02B 5/045
See application file for complete search history.

(56) References Cited

U.S. PATENT DOCUMENTS

| | | | | |
|---|---|---|---|---|
| 4,367,009 A | * | 1/1983 | Suzki | 359/204.1 |
| 5,942,432 A | * | 8/1999 | Smith et al. | 435/303.1 |
| 7,687,260 B2 | * | 3/2010 | Gutekunst | 435/288.7 |
| 2001/0046050 A1 | | 11/2001 | Hoyt | |
| 2002/0164114 A1 | | 11/2002 | Golub et al. | |
| 2003/0160957 A1 | * | 8/2003 | Oldham et al. | 356/317 |
| 2004/0014202 A1 | | 1/2004 | King et al. | |
| 2004/0023229 A1 | | 2/2004 | Rigler | |

OTHER PUBLICATIONS

PCT International Search Report and Written Opinion of the International Searching Authority mailed Jul. 1, 2010 for International Application No. PCT/US2009/066645 filed on Dec. 3, 2009.

* cited by examiner

*Primary Examiner* — Christopher M Babic
*Assistant Examiner* — Jeremy C Flinders
(74) *Attorney, Agent, or Firm* — McCarter & English, LLP; Maria Laccotripe Zacharakis

(57) ABSTRACT

The invention relates to optical systems and methods for measurement of samples in multiple sample vessels using an array of light sources where the light from the light sources is divided into multiple light beams, and each beam is directed to a sample vessel.

21 Claims, 5 Drawing Sheets

OPTICAL SYSTEM FOR MULTIPLE REACTIONS

CROSS-REFERENCE

The present application is the U.S. National Phase of International Application No. PCT/US2009/066,645, filed Dec. 3, 2009. This application also claims the benefit of U.S. Provisional Application No. 61/119,692, filed Dec. 3, 2008, which application is incorporated herein by reference in its entirety.

BACKGROUND OF THE INVENTION

Many laboratories including those involved in life science research often carry out multiple reactions simultaneously, for example, using reaction plates having multiple reaction vessels such as 24, 48, 96, or 386 wells. Carrying out reactions in plates can facilitate automation of laboratory processes. Many lab instruments are now adapted to receive multi-well plates for various operations such as heating and cooling and centrifugation.

In some cases, it is useful to be able to optically interrogate a set of samples while they are within the multi-well plate without having to transfer the samples to a separate optical instrument. It can be desirable to carry out reactions such as polymerase chain reaction (PCR), which require heating and cooling, and measure the extent of such reactions optically while the reaction is carried out without removing the samples from the plates, and without removing the plate from the heating and cooling system.

The advent of Polymerase Chain Reaction (PCR) in 1983 has revolutionized molecular biology through vastly extending the capability to identify, manipulate, and reproduce genetic materials such as DNA. Now, PCR is routinely practiced in medical and biological research laboratories for a variety of tasks, such as the detection of hereditary diseases, the identification of genetic fingerprints, the diagnosis of infectious diseases, the cloning of genes, paternity testing, and DNA computing. The method has been automated through the use of thermal stable DNA polymerases and machines capable of heating and cooling genetic samples rapidly, commonly known as thermal cyclers.

The optical measurements useful for interrogating these reactions can involve the measurement of fluorescence. To measure fluorescence, excitation light is directed at the samples in the sample vessels, and light emitted from the fluorophores in the samples is detected. It is often desirable that the transfer of light from the light source to the wells be carried out effectively and efficiently. Optical systems for directing light to sample plates is known, for example, as described in U.S. Pat. Nos. 6,942,837, 7,369,227, 6,852,986, and 7,410,793. While optical systems for directing light to sample vessels in plates and detecting light from the sample vessels are known. There is a need for optical systems which can so more effectively and efficiently.

SUMMARY OF THE INVENTION

One aspect of the invention comprises an apparatus for measuring the optical properties of a samples in sample vessels comprising: an array of n light sources; a holder adapted to mate with a sample plate comprising m sample vessels; an optical divider arranged such that light from each light source is divided into x light beams; a set of source optical components that deliver the light beams from the optical divider to the m sample vessels.

In some embodiments the light sources are light emitting diodes (LEDs). In some embodiments the optical divider is a prismatic optical divider.

In some embodiments $m/n=2$. In some embodiments $m/n=4$.

In some embodiments the apparatus further comprises an optical detector and a set of detector optical components arranged such that light from the m sample vessels is detected by the detector.

In some embodiments the source optical components comprise an excitation filter and the detector optical components comprise an emission filter. In some embodiments the holder adapted to mate with the sample plate comprises a heating element in thermal contact with the sample vessels.

One aspect of the invention comprises a method for measuring the optical properties of samples comprising: illuminating samples in an array of m sample vessels with an array of n light sources wherein light from the n light sources is divided into x light beams, such that n times x is m, and m light beams are produced; directing the m beams to the m sample vessels using optical components; measuring light from the m sample vessels at a detector.

In some embodiments the light sources are divided into beams with a prismatic optical divider.

In some embodiments the samples comprise a fluorescent agent, wherein the beams excite the fluorescent agent to produce fluorescent light, and wherein the light measured at the detector comprises said fluorescent light.

In some embodiments the method further comprises heating and cooling the samples to perform polynucleotide amplification and measuring the optical properties of the samples during or between cycles in order to determine the level of amplification.

In some embodiments the polynucleotide amplification comprises real time polymerase chain reaction.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Many features of the invention are set forth with particularity in the appended claims. A better understanding of the features and advantages of the invention will be obtained by reference to the following detailed description that sets forth illustrative embodiments, in which many principles of the invention are utilized, and the accompanying drawings of which:

DETAILED DESCRIPTION OF THE INVENTION

Figure 1:
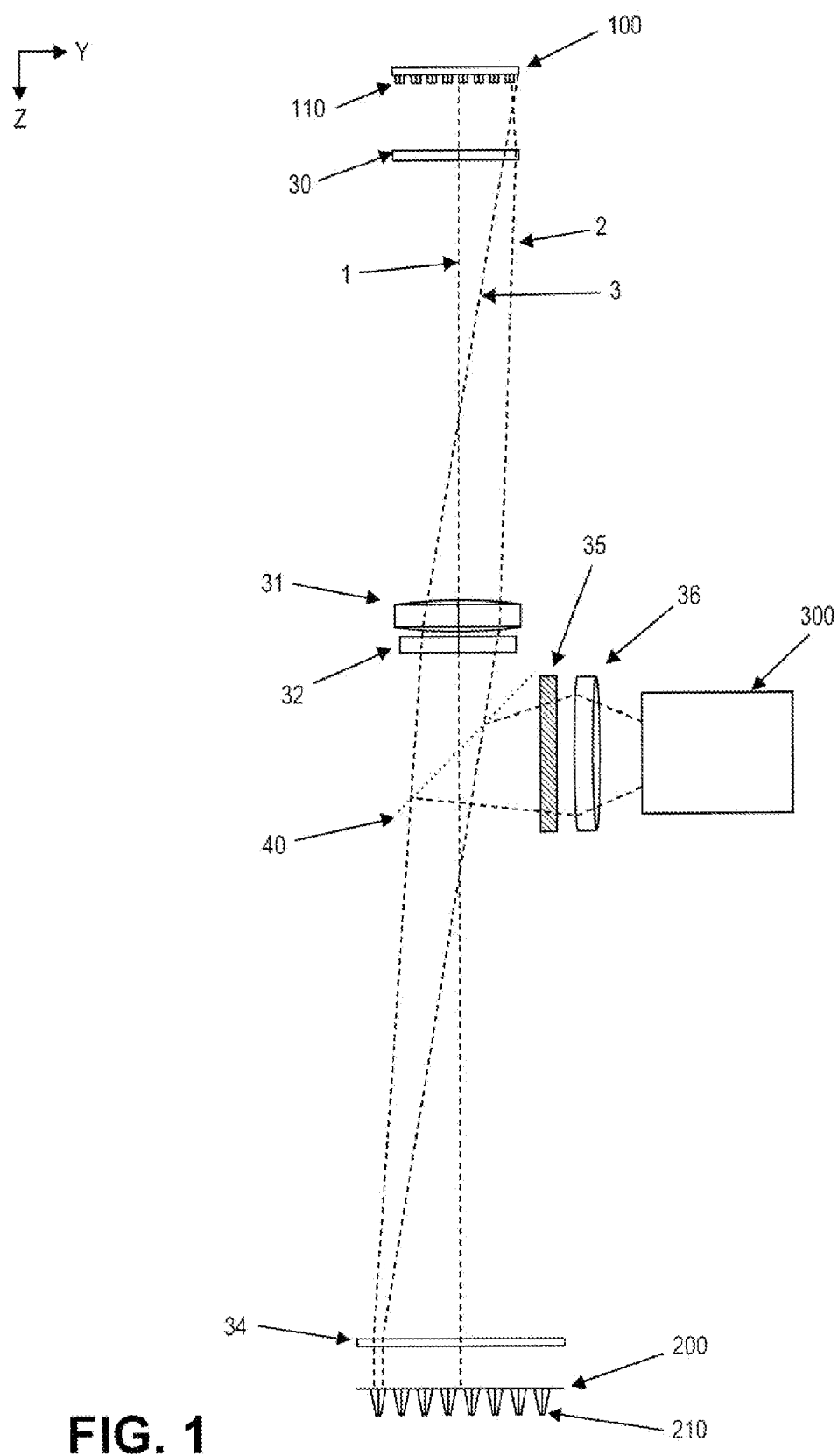
FIG. 1 shows an optical system known in the art.

Described herein are a devices, methods, and systems for measuring multiple chemical reactions in multiwell plates.

An optical assembly of systems herein can comprise multiple light sources, such as light emitting diodes (LEDs). In the optical assembly, each light source, for example LED, corresponds to a sample vessel on the multiwell plate.

Exemplary embodiments of the invention described herein utilize particular arrangements of optical elements such as lenses, filters, and reflectors. There are many other optical arrangements which can be implemented in order to carry out or construct the invention that would be understood by one of ordinary skill in the art for directing the light beams to the corresponding sample vessels and for directing light from the sample vessels to a detector.

Where the optical system has an excitation source array, a detector, and the appropriate filters, lenses, and reflectors, the system can be used as a fluorometer. A fluorometer provides excitation light to a sample and detects the light emitted from fluorescent entities within the sample.

Also disclosed herein are systems for the controlled heating of samples such as biological samples for thermal cycling reactions. The devices herein can offer improved temperature uniformity and distribution to current technology in the art. Temperature uniformity can be highly desirable in PCR reactions, for example, where a plurality of samples in a plurality of reaction containers must be cooled and heated simultaneously.

In addition to heating of PCR samples, the devices and methods herein can be used widely in the field of biotechnology and chemistry. Examples include but are not limited to incubations of enzymatic reactions such as restriction enzymes, biochemical assays and polymerase reactions; cell culturing and transformation; melting of nucleic acids; hybridization; and any treatment requiring precise temperature control. Based on the present disclosure, one of ordinary skill in the art can readily adapt the disclosed technology to various analyses of biological/chemical samples which require accurate temperature control.

In some instances, a system as described herein can further comprise an optical assembly having a light source and an optical detector, wherein the optical assembly is positioned such that light from the light source is directed into the sample holder, and light from the sample holder is detected by the detector. The detector of the optical assembly can comprise a PIN photodiode, a CCD imager, a CMOS imager, a line scanner, a photodiode, a phototransistor, a photomultiplier or an avalanche photodiode. The excitation source can comprises one or more LEDs, laser diodes, vertical cavity surface emitting lasers (VCSELs), vertical external cavity surface emitting lasers (VECSELs), or diode pumped solid state (DPSS) lasers. In some embodiments, the optical elements can be arrays of light emitting diodes (LEDs). LEDs have advantages as light sources for the optical systems of the invention in that they are small, relatively inexpensive, generate relatively low heat, and can provide light in the spectral ranges required for measuring samples, for example by fluorescence.

An optical detector as described herein can comprise a plurality of optical detectors, wherein at least one optical detector corresponds to a sample well in a sample microplate.

An apparatus herein can also further comprise a control assembly which controls the apparatus, the light source, and the detector. In some instances, the control assembly comprises a programmable computer programmed to automatically process samples, run multiple temperature cycles, obtain measurements, digitize measurements into data and convert data into charts or graphs.

The present invention concerns an optical system and methods for measuring multiple chemical reactions in multi-well plates. The optical system comprises multiple light sources, such as light emitting diodes (LED's). In the optical system of the present invention, each light source, e.g. LED, corresponds to more than one sample vessel on the multi-well plate. The light source is divided by an optical divider into multiple beams of light, and each of the light beams can be directed to a sample vessel on the multi-well plate. In order to divide the source into beams of light, a light divider is used. In some cases, the use of the light divider can result in more efficient use of the light. In some cases, the use of the light divider will result in using a wider solid angle of light emitted from the light source, so that multiple wells can each receive as much or almost as much light as the case where each light source is directed to one corresponding well.

The optical dividers of the present invention can be, for example, prismatic beam dividers, which can be easily produced, for example by injection molding of optical plastics. In some embodiments, the optical surfaces of the optical dividers, e.g. prismatic dividers, are substantially flat, and can be made relatively inexpensively without the need for extremely precise tolerances. The prismatic optical divider can have features on one face, or on both the top face and the bottom face. In other embodiments, arrays of lenses, mirrors, or other optical components can be used to divide the light from the light sources.

The optical systems and methods of the invention can result in the use of fewer light sources for the illumination of the sample vessels than is required where there is a one to one correspondence between light source and sample vessel. The use of fewer light sources can also result in simpler electronics. The use of fewer light sources can be beneficial in heat management, in that the light from the sources can be more effectively used than when the light is not divided.

FIG. 1 shows an optical system known in the art having a one to one correspondence between the light sources and the sample vessels on the multi-well plate. Shown here is a side view of an 8 by 4 array of light sources 100 which illuminates an 8 by 4 array of sample wells 200. Lenses and filters 30-34 direct the light from the light sources to the corresponding sample vessels on the multi-well plate. Rays 1, 2, and 3 show how the light from each light source 110 is directed to its corresponding sample vessel 210.

Figure 2:
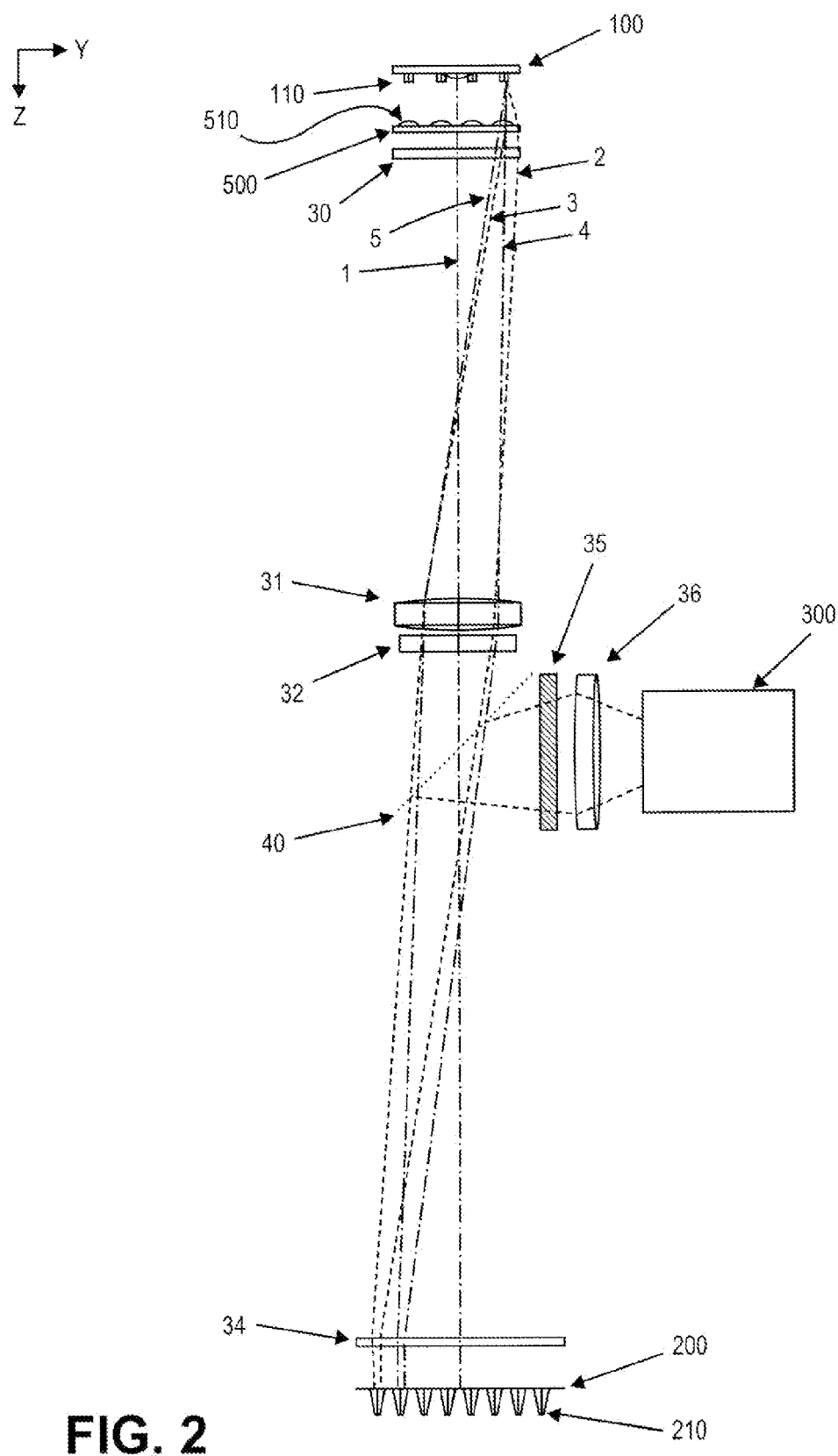
FIG. 2 shows an optical system of the present invention comprising an optical divider that produces two beams from each light source.

FIG. 2 shows an optical system of the present invention in which the light from each light source in the array is divided into two beams, each beam directed to a single sample vessel in the sample plate. The system shown in FIG. 2 illustrates an 8 by 4 array of sample vessels 210 in a sample plate 200 in which the sample vessels are illuminated with a 4 by 4 array 100 of light emitting diodes 110. The light from each of the LED's 110 is divided into two beams by the prismatic optical divider 500. In this embodiment, the prismatic optical divider has 4 prismatic ridges 510, each with a triangular cross-section. The paths of representative light rays are represented by the dashed lines in the figure. Ray 1 shows a light ray from the center of the LED Array 100 to the center of the plate 200. Rays 2-5 illustrate that the light from one light source 110 is divided into two light beams and the light from each divided light beam illuminating one sample vessel 210 with the result that one LED 110 illuminates two sample vessels 210. Rays 2-5 travel through the same prismatic ridge, but Rays 2 and 3 travel through the right face of the prismatic ridge 510, and thus are directed to the left-most sample vessel 210. Rays 4 and 5 travel through the left face of the prismatic ridge 510, and are directed to the sample vessel 210 adjacent to the sample vessel 210 to which rays 2 and 3 were directed. The division of the light from the other three LED's 210 in the row in a similar manner results in the illumination of 8 wells 210 by 4 LED's 110 in the LED array 100. The remaining 3 rows of 4 LED's, extending in the X direction of the figure (into the page) have their light divided analogously, thereby illuminating the remaining 3 rows of 8 sample vessels in the sample plate 200.

Figure 3:
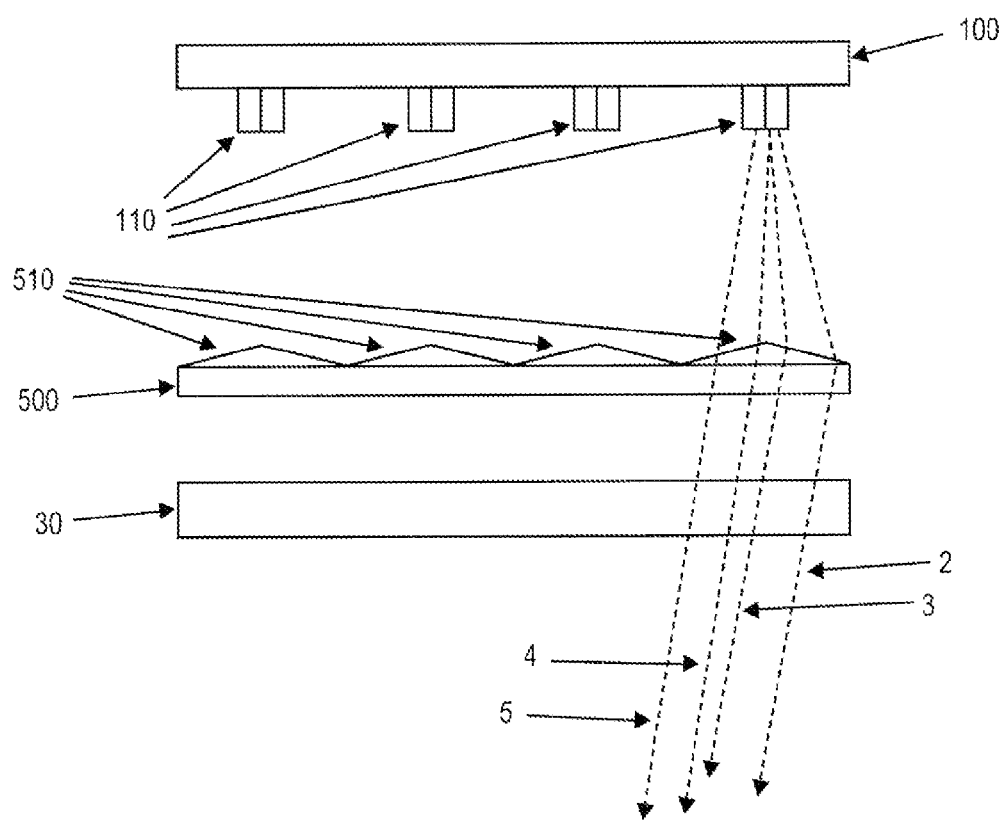
FIG. 3 shows a close up view of the top portion of the optical system of the invention shown in FIG. 2.

FIG. 3 shows a close up view of the upper portion of FIG. 2. The light from the LED's 110 is divided into two beams by the prismatic optical divider 500. The prismatic optical divider has 4 prismatic ridges 510 having triangular cross-sections. The paths of light rays are represented by the dashed lines in the figure. Rays 2-5 illustrate that the light from one light source 110 is divided into two light beams in order to illuminate two sample vessels with one light source. Rays 2, 3, 4 and 5 travel through the same prismatic ridge, but Rays 2 and 3 travel through the right face of the prismatic ridge 510. Rays 4 and 5 travel through the left face of the prismatic ridge 510, and are directed to a different sample vessel than the one to which rays 2 and 3 are directed. FIG. 3 also depicts field lens 30, which, as part of the optical system, directs the divided beams to their corresponding sample wells.

The optical system depicted in FIG. 2 also includes a detector 300 for detecting light from the sample vessels, and optical components 30-40 for directing the light in the system. The divided light beams from the prismatic divider 500 pass through field lens 30, imaging lens 31, excitation filter 32, dichroic reflector 40, and second field lens 34 directing the beams to the sample vessels 210.

Light from the sample vessels, for example light that is emitted from fluorescent dyes within the sample vessels is detected by the detector 300. The light from the sample vessels passes through the field lens 34, reflects off of the dichroic reflector 40, and passes through emission filter 35 and lens 36 into detector 300, where the light is detected.

Figure 4:
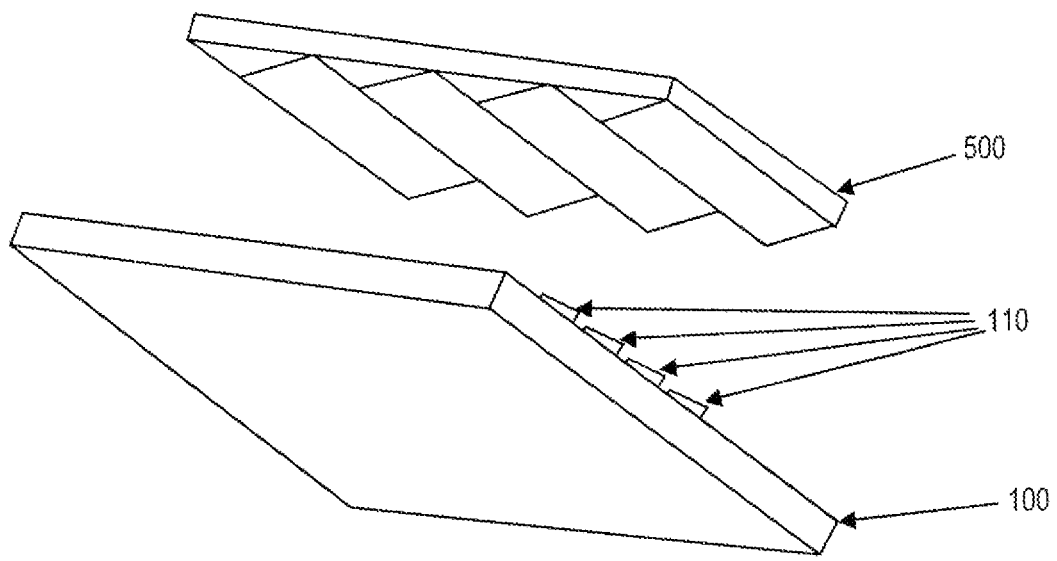
FIG. 4 shows a 3 dimensional representation of a light source array and optical divider of the invention where the optical divider produces two beams from each light source.

FIG. 4 shows a 3 dimensional representation of a light source array and optical divider of the invention where the optical divider produces two beams from each light source. In the embodiment shown, the optical divider 500 has ridges on one side, in this embodiment on the side closest to the light sources. In other embodiments the divider has prismatic ridges or other features on the optical divider furthest from the light sources.

Figure 5:
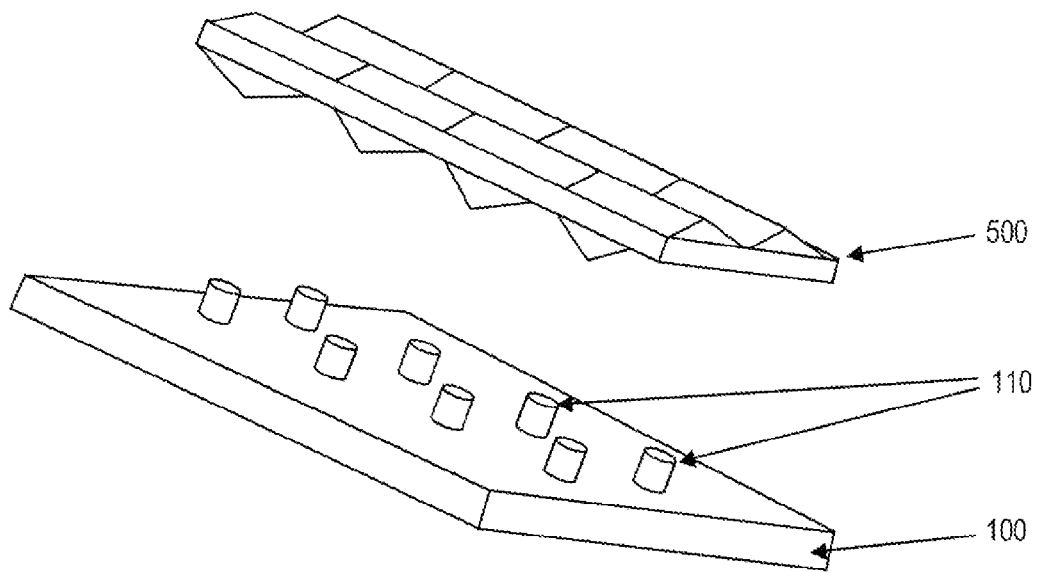
FIG. 5 shows 3 dimensional representation of a light source array and optical divider of the invention where the optical divider produces four beams from each light source.

FIG. 5 shows 3 dimensional representation of a light source array and optical divider of the invention where the optical divider produces four beams from each light source. In this embodiment, the optical divider 500 has optical features on both sides. In the embodiment shown, the optical divider has prismatic ridges on both sides. In other embodiments, the optical divider can have other optical features on both sides.

The embodiment of the invention shown above utlize a particular arrangement of optical elements such as lenses, filters, and reflectors. There are many other optical arrangements which can be implemented in order to carry out the present invention that would be understood by one of ordinary skill in the art for directing the divided light beams to the corresponding sample vessels and for directing light from the sample vessels to a detector. The optical arrangement can be on-axis as shown in FIG. 2, where the LED array is located directly above the sample vessel plate, and these elements are parallel and centered. In some embodiments the elements of the system can be off-axis. Off-axis embodiments such as those described in U.S. Pat. No. 7,109,495 can be used with the optical system of the present invention.

Where the optical system has a light source array, a detector, and the appropriate filters, lenses, and reflectors, the system can be used as a fluorimeter. A fluorimeter provides excitation light to a sample and detects the light emitted from fluorescent entities within the sample.

In some cases the system of the invention also comprises a thermal control unit or a thermal cycler to which the sample vessels in the multi-well plate can mate. The optical system of the present invention can be advantageous for measuring the state of reactions within the reaction vessels during and between reaction steps and cycles without having to remove the samples from the thermal cycling element. For example, the system can be used to measure polynucleotide amplification such as polymerase chain reaction (PCR) and real-time polymerase chain reaction (RT-PCR) amplifications.

In some embodiments the optical divider can divide the light from one light source into two beams, each divided beam directed to a different sample well on the plate. For example, the optical system of the present invention can comprise a light source array with 12 light sources illuminating a plate having 24 sample vessels, a light source array with 24 light sources illuminating a plate having 48 sample vessels, a light source array with 48 light sources illuminating a plate having 96 sample vessels, a light source array with 192 light sources illuminating a plate having 384 sample vessels, or a light source array with 786 light sources illuminating a plate having 1536 sample vessels The optical dividers of the invention can be used to divide the light from one light source into more than two beams. The optical dividers can be used to divide the light into 3, 4, 5, 6, 7, 8 or more beams. In some cases the optical dividers can result in more efficient use of the light generated by the light sources. In a conventional optical system, much of the light generated by the light source is lost as it is not captured by the optical system. While the light source generates light in a wide solid angle, only a portion of that solid angle will generally pass into the optical system. In some embodiments of the present invention, the optical divider allows for the collection and use of a wider solid angle of light from the light source, thus utilizing more of the light than in earlier described systems having a one to one correspondence of light source to sample vessel. In some cases, using the present optical system, multiple sample vessels can receive the same amount of light from a light source that a single sample vessel would receive from the same type of light source in a conventional system without an optical divider. For example, in some embodiments, one LED can be used to illuminate two sample vessels, and each vessel can receive as much light, or almost as much light as a single sample vessel would receive in a conventional system in which one LED corresponds to each sample vessel.

The light source can comprises one or more LEDs, laser diodes, vertical cavity surface emitting lasers (VCSELs), vertical external cavity surface emitting lasers (VECSELs), or diode pumped solid state (DPSS) lasers. In some embodiments, the optical elements can be arrays of light emitting diodes (LED's). LED's have advantages as light sources for the optical systems of the invention in that they are small, relatively inexpensive, generate relatively low heat, and can provide light in the spectral ranges required for measuring samples, for example by fluorescence. According to various embodiments, the excitation source can be a Light Emitting Diode (LED). The LED can be, for example, an Organic Light Emitting Diode (OLED), a Thin Film Electroluminescent Device (TFELD), or a Quantum dot based inorganic organic LED. The LED can include a phosphorescent OLED (PHOLED). As used herein, the terms excitation source and light source are used interchangeably.

In some instances, a light source can contain one Light Emitting Diode (LED) or an array of LEDs. According to various embodiments, each LED can be a high power LED that can emit greater than or equal to about 1 mW of excitation energy. In various embodiments, a high power LED can emit at least about 5 mW of excitation energy. In various embodiments wherein the LED or array of LEDs can emit, for example, at least about 50 mW of excitation energy, a cooling device such as, but not limited to, a heat sink or fan can be used with the LED. An array of high-powered LEDs can be used that draws, for example, about 10 watts of energy or less or about 10 watts of energy or more. The total power draw can depend on the power of each LED and the number of LEDs in the array. The use of an LED array can result in a significant reduction in power requirement over other light sources, such as, for example, a 75 watt halogen light source or a 150 watt halogen light source. Exemplary LED array sources are available. In some instances, LED light sources can use about 1 microwatt of power or less, for example, about 1 mW, about 5 mW, about 25 mW, about 50 mW, about 100 mW, about 500 mW about 1 W, about 5 W, about 50 W, or about 100 W or more, individually or when in used in an array. In some instances, the LED light sources use about 1 microwatt to about 100 W of power.

In some embodiments the optical divider can divide the light from one light source into four beams, each divided beam directed to a different sample well on the plate. In some cases, dividing into four beams can be accomplished with features on one side of the prismatic divider. For example, the prismatic divider can have features on one side of a prismatic plate with four fold symmetry, for example 4-sided pyramids. The 4-sided pyramid can provide four faces, each face capable of directing light from a light source.

In some embodiments, division of the light source into 4 beams can be accomplished with a prismatic plate having features on both the top and the bottom of the prismatic plate. For example, a prismatic plate can have a set of prismatic ridges on the top of the prismatic divider, and a set of perpendicular prismatic ridges on the bottom of to the prismatic divider.

Where the optical divider divides light into 4 beams, the optical system of the present invention can comprise a light source array with 6 light sources illuminating a plate having 24 sample vessels, a light source array with 12 light sources illuminating a plate having 48 sample vessels, a light source array with 24 light sources illuminating a plate having 96 sample vessels, a light source array with 48 light sources illuminating a plate having 384 sample vessels, or a light source array with 384 light sources illuminating a plate having 1536 sample vessels.

The optical system of the invention can utilize more than one light source array. For example, a set of 4 light source arrays, each having 12 light sources, each light source divided into two beams can be used to illuminate a sample plate with 96 sample vessels.

The detector can comprise a detector array comprising optical detection elements such as CCDs, CMOS, photodiodes, avalanche photodiodes, photomultiplier tubes (PMTs), PIN photodiodes, a line scanner, or phototransistors.

In some instances, an excitation source can be used to provide excitation beams to irradiate a sample solution containing one or more dyes. For example, two or more excitation beams having the same or different wavelength emissions can be used such that each excitation beam excites a different respective dye in the sample. The excitation beam can be aimed from the light source directly at the sample, through a wall of a sample container containing the sample, or can be conveyed by various optical systems to the sample. An optical system can include one or more of, for example, a mirror, a beam splitter, a fiber optic, a light guide, or combinations thereof.

The invention also comprises methods for measuring the optical properties of a sample in a multi-well plate comprising, for example, illuminating samples in multiple sample vessels with an array of light sources wherein light from the light sources is divided into beams; directing the beams using optical components to the sample vessels; and measuring light from the sample vessels at a detector.

In some cases the system of the invention also comprises a thermal control unit or a thermal cycler to which the sample vessels in the multiwell plate can mate. The optical system of the present invention can be advantageous for measuring the state of reactions within the reaction vessels during and between reaction steps and cycles without having to remove the samples from the thermal cycling element. For example, the system can be used to measure polynucleotide amplification such as polymerase chain reaction (PCR) and real-time polymerase chain reaction amplifications.

In embodiments described herein, the multiple temperature cycles correspond to multiple cycles of nucleic acid amplification. Nucleic acid amplification can comprise real-time PCR. For example, an apparatus or system of the invention can also be sometimes referred to as a thermal cycler.

In some instances, the heater is a thermoelectric device. In other instances, the heater is a resistive device. An apparatus herein can also comprise a cooler. In some instances, the heater and the cooler are the same device, for example, a Peltier device.

A variety of heaters and coolers are known to a practitioner in the art. In one embodiment, a heater is a Peltier device or a resistive heater. In an embodiment, the sample block is in thermal contact with a Peltier-effect thermoelectric device. In an alternative embodiment, the heater may be provided by extending a tube into the sample block through which hot or cold fluids can be pumped. In alternative embodiments, the sample block can be fitted with a heating and/or cooling coil, or with an electrical resistance heater arranged to prevent edge effects.

In an alternative embodiment, a heater and sometimes the reservoir is designed to maintain different temperatures in different zones of the reservoir wells. This can allow different sample wells in different zones to be cycled at different temperatures simultaneously. In one embodiment the liquid metal or thermally conductive fluid heat block is a capable of maintaining a temperature gradient across 2, 3, 4, 5, 6 or more zones. In one embodiment temperature gradients in excess of 0.1° C. to 20° C. across the reservoir can be achieved. In some embodiments the heat block will contain internal baffles or insulated walls which act to separate different zones of the liquid composition from other zones. Each zone may further comprise an individual fluid stirrer. Further each zone of the heat block may comprise individual heating and/or cooling elements such as a heat conduction element (wires, tubes), thin foil type heater, Peltier elements or cooling units.

As described herein, the sample holder can be a multiwell plate. In some instances, the multiwell plate has 16, 24, 48, 96, 384 or more sample wells. In some instances, the multiwell plate is a standard microwell plate for biological analysis. For example, the multiwell plate can be plate used for PCR. In an embodiment, the multiwell plate consists of 48 sample wells. The apparatus described herein can function to keep the temperature of the samples within each of the sample wells of a multiwell plate within ±0.3° C. In other embodiments, the sample holder can be sample tubes, such as Eppendorf tubes.

As described herein, a sample holder can be reaction vessels of a variety of shapes and configurations. In an embodiment sample holder can be used to contain reaction mixtures, such as PCR reaction mixtures, reverse transcription reaction mixtures, real-time PCR reaction mixtures, or any other reaction mixture which requires heating, cooling or a stable uniform temperature. In one embodiment the sample holder is round or tubular shaped vessels. In an alternative embodiment the sample holder is oval vessels. In another embodiment the sample holder is rectangular or square shaped vessels. Any of the preceding embodiments may further employ a tapered, rounded or flat bottom. In yet another embodiment the sample holder is capillary tubes, such as clear glass capillary tubes or coated capillary tubes, wherein the coating (for example metal) increases internal reflectivity. In an additional embodiment the sample holder is slides, such as glass slides. In another embodiment the sample holder is sealed at the bottom. In another embodiment the sample holder is coated, at least internally, with a material for preventing an amplicon from sticking to the sample holder walls, such as a fluorinated polymer or BSA.

In one embodiment the sample holder is manufactured and used as individual vessels. In another embodiment the sample holder is a plurality of vessels linked together in a horizontal series comprising a multiple of individual vessels, such as 2, 4, 6, 10, 12, 14 or 16 tubes. In yet another embodiment the sample holder is linked together to form a sheet, plate or tray of vessels designed to fit into the top of the heating block of a thermal cycler so as to occupy some or all available reaction wells. In one embodiment the holder is a microplate comprising at least 6, wells, 12 wells, 24 wells, 36 wells, 48 wells, 54 wells, 60 wells, 66 wells, 72 wells, 78 wells, 84 wells, 90 wells or 96 wells, 144 wells, 192 wells, 384 wells, 768, or 1536 wells.

In one embodiment the sample holder has caps or a cover attached to the open ends of sample wells or vessels. In one embodiment the sample wells or vessels are designed to hold a maximum sample volume, such as 10 ul, 20 ul , 30 ul, 40 ul, 50 ul, 60 ul, 70 ul, 80 ul, 90 ul, 100 ul, 200 ul, 250 ul, 500 ul, 750 ul, 1000ul, 1500 ul, 2000 ul, 5 mL, or 10 mL.

In some embodiments real-time polymerase chain reactions (PCR) are performed in a sample holder manufactured from materials chosen for their optical clarity and for their known non-interaction with the reactants, such as glass or plastic. In one embodiment the sample holder is designed so that light can enter and leave through the top portion of the sample wells, which may be covered with a material at least partially transparent to light. In one embodiment the sample holder is designed so that light is directed to exit through a single surface, such as the top or bottom.

In other embodiments the sample holder is manufactured from materials that are substantially internally reflective, such as reflective plastic, coated plastic (such as with metal or other reflective substances), coated glass (such as with metal or other reflective substances), doped glass (manufactured with the addition of molecules that increase the reflectivity of the glass), or metal, including but not limited to stainless steel, chromium, or other substantially non-reactive metals.

In an aspect, a method of heating a biological sample comprises: positioning a sample holder containing a biological sample into thermal contact with an apparatus as described herein; and heating the biological sample contained by the sample holder with the apparatus.

In an embodiment, the method comprises performing PCR on the biological sample. The heating can comprises thermally cycling the biological sample between about 50-65° C. and about 90 to 100° C. PCR processes and methods are discussed in further detail herein.

In various embodiments a control assembly is operatively linked to an apparatus or thermal cycler of the invention. Such a control assembly, for example, comprises a programmable computer comprising computer executable logic that functions to operate any aspect of the devices, methods and/or systems of the invention. For example, the control assembly can turn on/off or actuate motors, fans, regulating circuits, stir bars, continuous flow devices and optical assemblies. The control assembly can be programmed to automatically process samples, run multiple PCR cycles, obtain measurements, digitize measurements into data, convert data into charts/graphs and report.

Computers for controlling instrumentation, recording signals, processing and analyzing signals or data can be any of a personal computer (PC), digital computers, a microprocessor based computer, a portable computer, or other type of processing device. Generally, a computer comprises a central processing unit, a storage or memory unit that can record and read information and programs using machine-readable storage media, a communication terminal such as a wired communication device or a wireless communication device, an output device such as a display terminal, and an input device such as a keyboard. The display terminal can be a touch screen display, in which case it can function as both a display device and an input device. Different and/or additional input devices can be present such as a pointing device, such as a mouse or a joystick, and different or additional output devices can be present such as an enunciator, for example a speaker, a second display, or a printer. The computer can run any one of a variety of operating systems, such as for example, any one of several versions of Windows, or of MacOS, or of Unix, or of Linux.

In some embodiments, the control assembly executes the necessary programs to digitize the signals detected and measured from reaction vessels and process the data into a readable form (for example, table, chart, grid, graph or other output known in the art). Such a form can be displayed or recorded electronically or provided in a paper format.

In some embodiments, the control assembly controls regulating circuits linked to the thermal elements so as to regulate/control cycles of temperatures of an apparatus as described herein.

In further embodiments, for example in real-time PCR, the control assembly generates the sampling strobes of the optical assembly, the rate of which is programmed to run automatically. The timing can be adjustable for shining a light sources and operating a detector to detect and measure signals (for example, fluorescence).

In another embodiment an apparatus comprising a control assembly further comprises a means for moving sample vessels into apertures, such as wells in the receptacle of a heat block comprising a liquid composition. In an embodiment said means could be a robotic system comprising motors, pulleys, clamps and other structures necessary for moving sample vessels.

In some aspects of the invention, the devices/systems of the invention are operatively linked to a robotics sample preparation and/or sample processing unit. For example, a control assembly can provide a program to operate automated collection of samples, adding of reagents to collection tubes, processing/extracting nucleic acids from said tubes, optionally transferring samples to new tubes, adding necessary reagents for a subsequent reaction (for example, PCR or sequencing), and transferring samples to a thermal cycler according to the invention.

A system as configured herein can be used for disease diagnosis, drug screening, genotyping individuals, phylogenetic classification, environmental surveillance, parental and forensic identification amongst other uses. Further, nucleic acids can be obtained from any source for experimentation. For example, a test sample can be biological and/or environmental samples.

Biological samples may be derived from human, other animals, or plants, body fluid, solid tissue samples, tissue cultures or cells derived therefrom and the progeny thereof, sections or smears prepared from any of these sources, or any other samples suspected to contain the target nucleic acids. Exemplary biological samples are body fluids including but not limited to blood, urine, spinal fluid, cerebrospinal fluid, sinovial fluid, ammoniac fluid, semen, and saliva. Other types of biological sample may include food products and ingredients such as vegetables, dairy items, meat, meat by-products, and waste. Environmental samples are derived from environmental material including but not limited to soil, water, sewage, cosmetic, agricultural, industrial samples, air filter samples, and air conditioning samples.

An apparatus herein can be used in any protocol or experiment that requires either thermal cycling or a heat block that can accurately maintain a uniform temperature. For example said thermal cycler can be used for polymerase chain reaction (PCR), quantitative polymerase chain reaction (qPCR), nucleic acid sequencing, ligase chain polymerase chain reaction (LCR-PCR), reverse transcription PCR reaction (RT-PCR), single base extension reaction (SBE), multiplex single base extension reaction (MSBE), reverse transcription, and nucleic acid ligation.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus for measuring the optical properties of a samples in sample vessels, the apparatus comprising:
   (a) an array of n light sources;
   (b) a holder adapted to mate with a sample plate comprising m sample vessels, wherein the holder adapted to mate with the sample plate comprises a heating element in thermal contact with the sample vessels;
   (c) an optical divider comprising a prismatic optical divider and arranged such that light from each light source is divided into x light beams wherein each of the light beams comprise the same wavelength of light; and
   (d) a set of source optical components that deliver the light beams from the optical divider to the m sample vessels.

2. The apparatus of claim 1 wherein the light sources comprise light emitting diodes (LEDs).

3. The apparatus of claim 1 wherein m/n=2.

4. The apparatus of claim 1 wherein m/n=4.

5. The apparatus of claim 1 further comprising an optical detector and a set of detector optical components arranged such that light from the m sample vessels is detected by the detector.

6. The apparatus of claim 5 wherein the source optical components comprise an excitation filter and the detector optical components comprise an emission filter.

7. A method for measuring the optical properties of samples, the method comprising:
   a) heating and cooling the samples to perform polynucleotide amplification; and
   b) measuring the optical properties of the samples during the amplification in order to determine the level of amplification, wherein the measuring of the optical properties of the samples comprises:
      i) illuminating samples in an array of sample vessels with an array of n light sources, wherein a holder is adapted to mate with a sample plate which includes the array of sample vessels, and wherein light from the n light sources is divided into x light beams with a prismatic optical divider, such that n times x is m, and m light beams are produced;
      ii) directing the m beams to the m sample vessels using optical components; and
      iii) measuring light from the m sample vessels at a detector.

8. The method of claim 7 wherein the samples comprise a fluorescent agent, wherein the beams excite the fluorescent agent to produce fluorescent light, and wherein the light measured at the detector comprises said fluorescent light.

9. The method of claim 7 wherein the polynucleotide amplification comprises real time polymerase chain reaction.

10. The method of claim 9, wherein the samples comprise a fluorescent agent, wherein the beams excite the fluorescent agent to produce fluorescent light, and wherein the light measured at the detector comprises said fluorescent light.

11. An apparatus for measuring the optical properties of samples in sample vessels, the apparatus comprising:
   a) an array of n light sources;
   b) a holder adapted to mate with a sample plate comprising m sample vessels;
   c) an optical divider comprising a prismatic optical divider and arranged such that light from each light source is divided into x light beams wherein each of the light beams comprise the same wavelength of light;
   d) a set of source optical components that deliver the light beams from the optical divider to the m sample vessels; and
   e) an optical detector and a set of detector optical components arranged such that light from the m sample vessels is detected by the detector; wherein the source optical components comprise an excitation filter and the detector optical components comprise an emission filter.

12. The apparatus of claim 11, wherein the light sources comprise light emitting diodes (LEDs).

13. The apparatus of claim 11, wherein m/n=2.

14. The apparatus of claim 11, wherein m/n=4.

15. The apparatus of claim 1, wherein the prismatic optical divider comprises one or more prismatic ridges.

16. The apparatus of claim 15, wherein the one or more prismatic ridges are located on one surface of the prismatic optical divider.

17. The apparatus of claim 15, wherein the one or more prismatic ridges are located on both an upper surface and a lower surfaces of the prismatic optical divider.

18. The apparatus of claim 11, wherein the prismatic optical divider comprises one or more prismatic ridges.

19. The apparatus of claim 18, wherein the one or more prismatic ridges are located on one surface of the prismatic optical divider.

20. The apparatus of claim 18, wherein the one or more prismatic ridges are located on both an upper surface and a lower surfaces of the prismatic optical divider.

21. The apparatus of claim 11 wherein the holder adapted to mate with the sample plate comprises a heating element in thermal contact with the sample vessels.

* * * * *